United States Patent
Smith

(10) Patent No.: US 9,561,336 B2
(45) Date of Patent: Feb. 7, 2017

(54) DOSE UNIT, PACK OF DOSE UNITS AND INHALER FOR INHALATION OF COMBINATION OF DRUGS

(75) Inventor: Ian Smith, Great Abington (GB)

(73) Assignee: PFIZER LIMITED, Cambridgeshire (GB)

( * ) Notice: Subject to any disclaimer, the term of this patent is extended or adjusted under 35 U.S.C. 154(b) by 1034 days.

(21) Appl. No.: 13/380,083

(22) PCT Filed: Jun. 24, 2010

(86) PCT No.: PCT/IB2010/052888
§ 371 (c)(1),
(2), (4) Date: Dec. 22, 2011

(87) PCT Pub. No.: WO2011/004287
PCT Pub. Date: Jan. 13, 2011

(65) Prior Publication Data
US 2012/0111327 A1    May 10, 2012

Related U.S. Application Data

(60) Provisional application No. 61/223,441, filed on Jul. 7, 2009.

(51) Int. Cl.
*A61M 15/00*    (2006.01)

(52) U.S. Cl.
CPC ..... *A61M 15/0045* (2013.01); *A61M 15/0003* (2014.02); *A61M 15/0031* (2014.02);
(Continued)

(58) Field of Classification Search
USPC ............ 128/203.12, 203.14, 203.15, 203.21, 128/203.25
See application file for complete search history.

(56) References Cited

U.S. PATENT DOCUMENTS

2005/0154491 A1    7/2005  Anderson et al. ............ 700/236
2006/0120969 A1*   6/2006  Nilsson et al. ................ 424/46
(Continued)

FOREIGN PATENT DOCUMENTS

WO        03035599       5/2003
WO     WO2004011070     2/2004
(Continued)

OTHER PUBLICATIONS

"Drug". Miriam-Webster's Online Dictionary. Apr. 2, 2007. http://web.archive.org/web/20070402001556/http://www.merriam-webster.com/dictionary/drug.*
(Continued)

*Primary Examiner* — Justine Yu
*Assistant Examiner* — Kathrynn Lyddane
(74) *Attorney, Agent, or Firm* — Kramer Amado P.C.

(57) ABSTRACT

Various embodiments relate to a dose unit for a dry powder inhaler including: a dose carrier including a plurality of pockets each adapted to contain a dose of medication powder suitable for inhalation, the pockets being sequentially arranged such that the content of the pockets can be sequentially exposed to a flow of air for successive inhalations and a plurality of medication powder doses arranged in the pockets of the dose carrier. The doses are regularly distributed in the pockets according to a sequence of identical groups, each group including at least one blank pocket and one pocket containing a dose of medication powder. Various embodiments also relate to a pack including one such dose unit and one further dose unit with all pockets containing a medication powder. Various embodiments further relate to a dry powder inhaler including such a pack of dose units.

19 Claims, 3 Drawing Sheets

(52) U.S. Cl.
CPC .... *A61M 15/0048* (2014.02); *A61M 15/0051* (2014.02); *A61M 15/0061* (2014.02); *A61M 2202/064* (2013.01)

(56) References Cited

U.S. PATENT DOCUMENTS

| | | | |
|---|---|---|---|
| 2006/0191534 A1* | 8/2006 | Hickey et al. | 128/203.15 |
| 2007/0163581 A1 | 7/2007 | Braithwaite | 128/203.21 |
| 2007/0181124 A1* | 8/2007 | Casper et al. | 128/203.15 |
| 2008/0283057 A1 | 11/2008 | Rohrschneider et al. | 128/203.15 |
| 2010/0139655 A1* | 6/2010 | Genosar et al. | 128/203.15 |

FOREIGN PATENT DOCUMENTS

| | | |
|---|---|---|
| WO | 2004032921 | 4/2004 |
| WO | WO2005002654 | 1/2005 |
| WO | 2005080313 | 9/2005 |
| WO | 2005080324 | 9/2005 |
| WO | 2005090287 | 9/2005 |
| WO | 2005092840 | 10/2005 |
| WO | 2007010356 | 1/2007 |
| WO | 2007034325 | 3/2007 |
| WO | 2007107828 | 9/2007 |
| WO | 2008035157 | 3/2008 |
| WO | 2008041095 | 4/2008 |
| WO | 2009034432 | 3/2009 |

OTHER PUBLICATIONS

International Search Report PCT/IP2010/052888 dated Oct. 5, 2010.

* cited by examiner

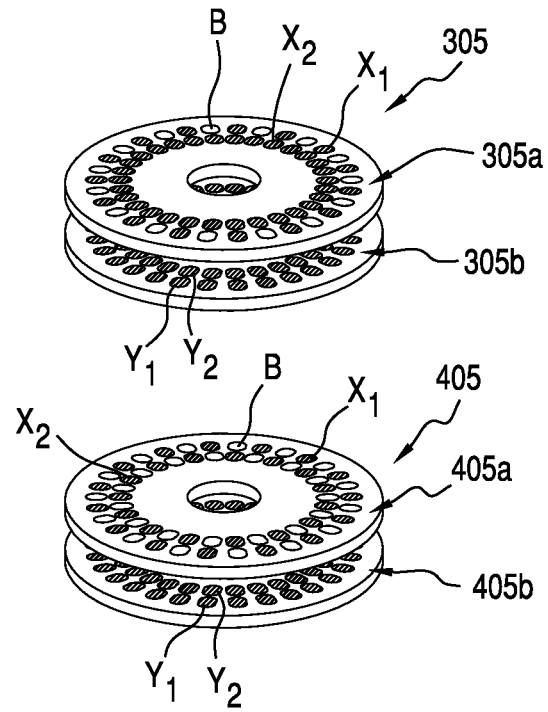
FIG. 6
FIG. 7
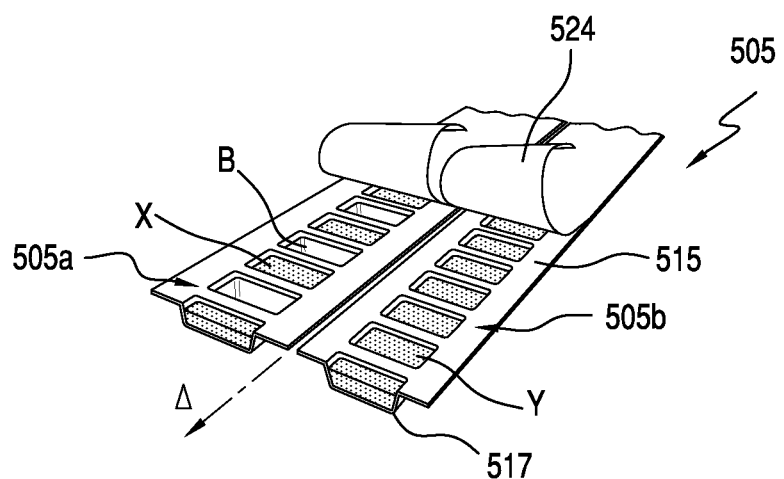
FIG. 8

DOSE UNIT, PACK OF DOSE UNITS AND INHALER FOR INHALATION OF COMBINATION OF DRUGS

This application is the National Stage Application of International Patent Application No. PCT/IB2010/052888, filed Jun. 24, 2010, which claims priority to U.S. Provisional Patent Application No. 61/223,441, filed on Jul. 7, 2009.

BACKGROUND OF THE INVENTION

The invention relates to a dose unit for a dry powder inhaler comprising:
- a dose carrier including a plurality of pockets each adapted to contain a dose of medication powder suitable for inhalation, said pockets being sequentially arranged such that the content of the pockets can be sequentially exposed to a flow of air for successive inhalations and
- a plurality of medication powder doses arranged in pockets of the dose carrier.

Typically, all pockets of such dose units contain a medication dose including a blend of at least one pharmaceutically active ingredient and at least one excipient. It has already been proposed to use a pair of such dose units in the same inhaler and more specifically to provide inhalers adapted to deliver medication powders from both units simultaneously. Such embodiments are for example described in WO 2005/002654 and WO 2004/011070. In particular embodiments known from such references, the first dose unit contains a first medication powder and the second dose unit contains a second medication powder different from the first one, whereby the inhaler can be used to deliver a combination of pharmaceutically active ingredients stored in separate carriers. This is of particular interest in certain therapies, for administering to the patient pharmaceutically active ingredients which must be delivered in combination but stored separately for stability reasons.

However, it might be desirable to administer to the patient not only the combination of the two medication powders but also, alternatively, only one of the two medication powders, in case the two medications must be administered at a different frequency. For example, it might be desirable to administer the first medication powder four times a day (QID) and the second medication powder twice in a day (BID).

With the known dose units and associated inhalers, this cannot be achieved with a single inhaler and the patient would rather have to alternatively use a first inhaler to inhale the first medication powder and a second inhaler to inhale the combination of the first and second medication powders.

This method is not only inconvenient but also confusing for the patient, whereby it may increase the risk of incorrect dosing.

It is an object of the invention to solve the aforementioned problem and allow the delivery of a plurality of inhalable drugs for combined treatments at different frequencies by means of a single inhalation device.

SUMMARY OF THE INVENTION

This is achieved by the dose unit according to the invention, wherein the doses are regularly distributed in the pockets according to a sequence of identical groups, each group including at least one blank pocket and one pocket containing a dose of medication powder.

Each blank pocket may be an empty pocket or, alternatively, a pocket containing an excipient powder.

According to a first embodiment of the invention, the dose carrier comprises a disc-shaped supporting structure and the pockets are held in an annular arrangement in the supporting structure, said supporting structure being adapted to be rotatably mounted in the dry powder inhaler so as to sequentially expose the content of the pockets.

Preferably, the disc-shaped supporting structure includes an annular arrangement of through holes and the dose carrier further comprises rigid inserts defining the pockets, each of said inserts being slidably accommodated in the respective through-hole in a storage position and is adapted to be displaced from said storage position into a dispensing position projecting from the disc-shaped supporting structure wherein the content of the pocket is exposed to the airflow.

According to a second embodiment of the invention, the dose carrier comprises an elongated strip formed with successive cavities defining the pockets arranged along the main direction of the strip.

Preferably, said elongated strip is flexible and shaped into a winding whereby the strip is adapted to be unwound in the dry powder inhaler so as to sequentially expose the content of the pockets.

Each of said identical groups may be constituted of one pocket containing a dose of medication powder and one blank pocket, whereby the pockets of the dose unit are alternatively blank and inclusive of a dose of medication powder.

The medication powder may include a single pharmaceutically active ingredient, said single pharmaceutically active ingredient being preferably selected from the group consisting of muscarinic M3 receptor agonists or anticholinergic agents, β2-adrenoceptor agonists, compounds having a dual muscarinic antagonist and β2-agonist activity and glucocorticoid receptor agonists.

More specifically, said single pharmaceutically active ingredient may be selected from the group consisting of ipratropium, tiotropium, oxitropium, trospium, aclidiniums, perenzepine, telenzepine, ephedrine, adrenaline, isoprenaline, metaproterenol, phenylephrine, phenylpropanolamine, pirbuterol, reproterol, rimiterol, isoetharine, carmoterol, albuterol, terbutaline, bambuterol, fenoterol, salbutamol, tulobuterol formoterol, salmeterol, prednisone, prednisolone, flunisolide, triamcinolone acetonide, beclomethasone, budesonide, fluticasone, ciclesonide, mometasone as well as salts and/or solvates thereof.

Alternatively, the medication powder may include a combination of pharmaceutically active ingredients, preferably a combination of a β2-adrenoceptor agonist and a glucocorticoid receptor agonist.

More specifically, said combination of pharmaceutically active ingredients may be a combination of salmeterol xinafoate and fluticasone propionate or a combination of budesonide and formoterol fumarate dehydrate.

The invention also relates to a pack including a first dose unit as described above and a second dose unit for a dry powder inhaler comprising
- a dose carrier including a plurality of pockets adapted to contain a dose of a medication powder suitable for inhalation, said pockets being sequentially arranged such that the content of the pockets can be sequentially exposed to a flow of air for successive inhalations and
- a plurality of medication powder doses arranged in the respective pockets of the dose carrier such that all the pockets of the second dose unit are inclusive of a medication powder dose.

Advantageously, the dose carrier of the first dose unit and the dose carrier of the second dose unit have an identical distribution of pockets.

The medication powder of the second dose unit may include a single pharmaceutically active ingredient, preferably selected from the group consisting of muscarinic M3 receptor agonists or anticholinergic agents, β2-adrenoceptor agonists, compounds having a dual muscarinic antagonist and β2-agonist activity and glucocorticoid receptor agonists.

More specifically, said single pharmaceutically active ingredient may be selected from the group consisting of ipratropium, tiotropium, oxitropium, trospium, aclidiniums, perenzepine, telenzepine, ephedrine, adrenaline, isoprenaline, metaproterenol, phenylephrine, phenylpropanolamine, pirbuterol, reproterol, rimiterol, isoetharine, carmoterol, albuterol, terbutaline, bambuterol, fenoterol, salbutamol, tulobuterol formoterol, salmeterol, prednisone, prednisolone, flunisolide, triamcinolone acetonide, beclomethasone, budesonide, fluticasone, ciclesonide, mometasone as well as salts and/or solvates thereof.

Alternatively, the medication powder of the second dose unit may include a combination of pharmaceutically active ingredients.

The invention also relates to a dry powder inhaler for administering medication powder to a patient, comprising a pack as described above and means for simultaneously exposing in an inhalation airflow the respective contents of a pocket of the first dose unit and a corresponding pocket of the second dose unit.

BRIEF DESCRIPTION OF THE DRAWINGS

Preferred embodiments of the invention will now be described in more details, by way of example only, with reference to the accompanying drawings, which are not drawn to scale and wherein:

FIG. 4-7 show different versions of a pack of dose units suitable for the inhaler of FIG. 1 in accordance with the invention illustrating a variety of patterns of distribution of medication doses in; and FIG. 8 is a perspective view of a pack of dose units according to a second embodiment of the invention, with a peelable lid of the dose carrier illustrated in an open position.

DETAILED DESCRIPTION

Figure 1:
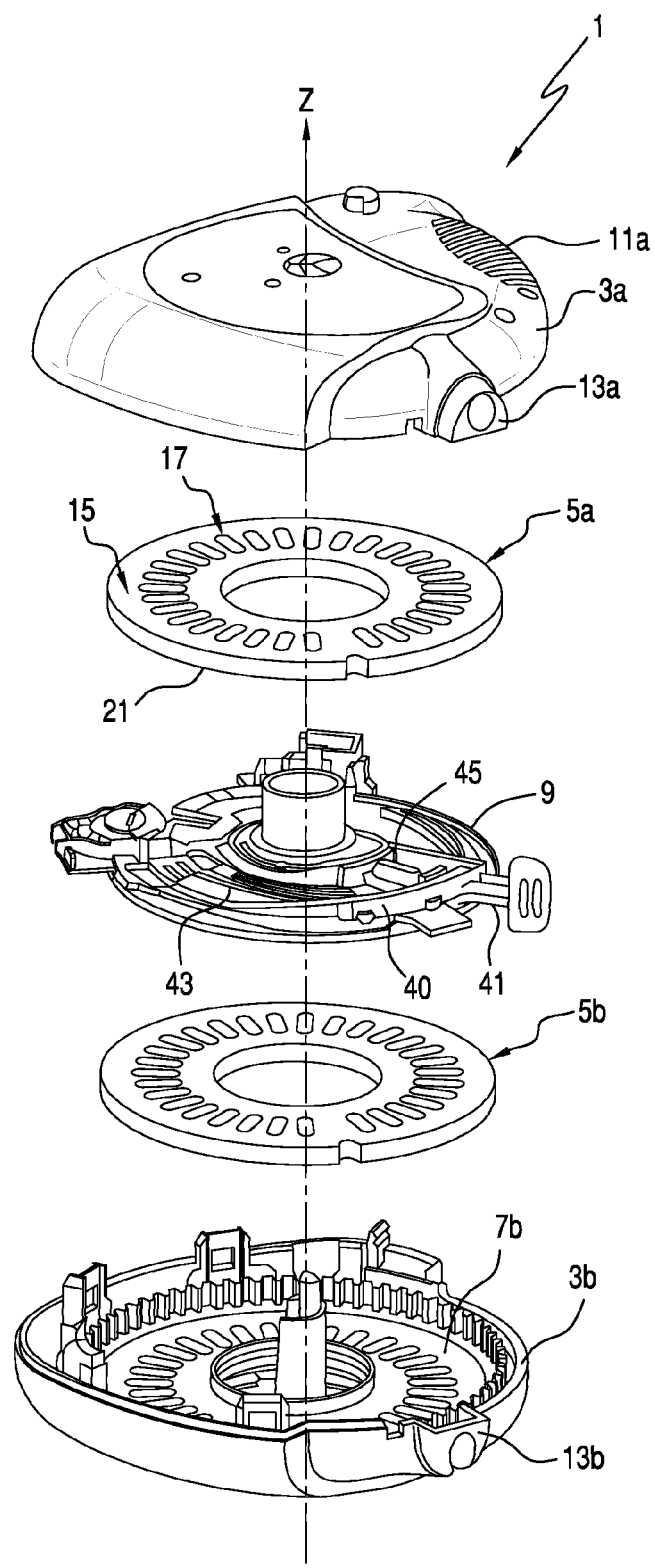
FIG. 1 is an exploded view of a dry powder inhaler of a type adapted to include a pack of dose units according to a first embodiment of the invention.
Figure 2:
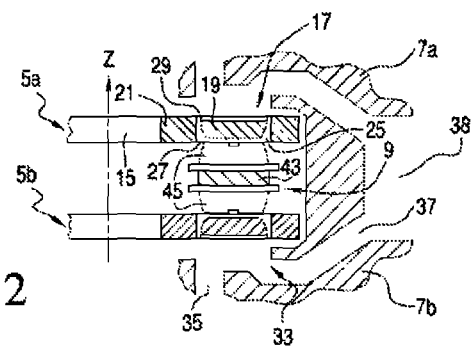
FIG. 2 is an enlarged partial and schematic cross-sectional view of the inhaler of FIG. 1, showing one pocket of each dose unit in the storage position before inhalation.
Figure 3:
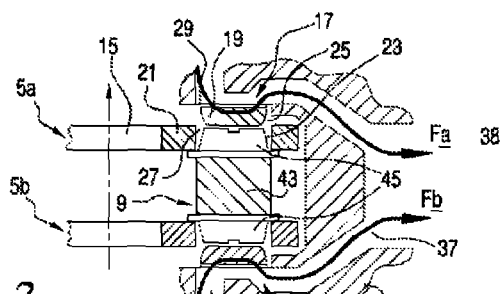
FIG. 3 is a similar view showing the pockets in the dispensing position during inhalation.

FIG. 1-3 illustrate a dry powder inhaler 1 from which a patient may inhale consecutive doses of medicament in the form of dry powder, said inhaler being of a type known from the aforementioned patent application WO 2005/002654 and adaptable to a first preferred embodiment of the present invention which is illustrated in FIG. 4-7.

In FIG. 1, the inhaler 1 is shown in a view exploded along a main axis Z of the inhaler. This axis Z is arbitrarily represented vertical on the drawings but this orientation is not supposed to reflect the orientation of the device in real conditions of use. Terms depicting position or orientation such as "axial" and "radial" should be interpreted, in the present description, with reference to this axis Z.

The inhaler 1 mainly includes a housing made of a pair of complementary shells 3a, 3b, a pair of dose units 5a, 5b, a pair of supports (only one 7b of which is visible on FIG. 1) defining an internal structure 7 (FIGS. 2 and 3) for accommodating the dose units 5a, 5b and a mechanism 9 operable by the patient to activate the inhaler.

Reference being more specifically made to FIG. 1, the housing comprises air intakes formed of apertures in the shells 3a, 3b constitutive of the housing. Only the apertures 11a formed on the shell 3a are visible on FIG. 1. The housing 3a, 3b further includes a mouthpiece made of two halves 13a, 13b, each formed on a respective shell.

As illustrated in FIG. 1-3, the dose units 5a, 5b each comprise a dose carrier 15 provided with a plurality of pockets 17, said pockets being each adapted to contain a dose of medication powder suitable for inhalation, and a plurality of medication powder doses 19 (FIGS. 2 and 3) arranged in pockets 17 of the dose carrier 15.

In the present patent application, the expression "medication powder dose" should be understood as a dose of powder which is suitable for inhalation by a patient and which includes at least one pharmaceutically active ingredient. Typically, as specified in the preamble of the present description, the medication powder is made of a blend of particles of one or more pharmaceutically active ingredient(s) with particles of one or more excipient(s). Such formulation is often designated as dry powder formulation. In contrast, in the context of the present description, a dose of powder containing excipient(s) but no pharmaceutically active ingredient should not be considered as a "medication powder dose".

The pharmaceutically active ingredient according to the present invention may be selected from any class of drugs which is suitable to the treatment or prevention of diseases, disorders and conditions by inhalation. Example of such diseases, disorders and conditions include for example allergic, inflammatory and/or respiratory disorders such as rhinitis, sinusitis, asthma, wheezy infant syndrome, bronchiolytis, bronchitis, bronchopneumopathy, nasal polyps, chronic obstructive pulmonary disease (COPD), pulmonary emphysema, acute respiratory distress syndrome (ARDS), cystic fibrosis, interstitial lung diseases, pulmonary fibrosis bronchospasm, lung hypersensitivity, exacerbation of airways hyper-reactivity consequent to other drug therapy, pulmonary hypertension, pneumonia, pulmonary embolism, tuberculosis, common cold, influenza, pharyngitis, lung cancer, etc. . . .

The pharmaceutically active ingredient(s) according to the present invention may thus be selected from numerous classes of medications such as for example glucocorticoid receptor agonists, PDE inhibitors in particular PDE4 inhibitors, sodium cromoglycate, muscarinic M3 receptor antagonists or anticholinergic agents, β2-adrenoceptor agonists, compounds having a dual muscarinic antagonist and β2-agonist activity, anti-tumour necrosis factor (anti-TNF-α) agents, adenosine A2a receptor agonists and A2b antagonists, histamine H3 antagonists and H4 antagonists, modulators of prostaglandin D2 including DP1 antagonists, DP2 antagonists and inhibitors of haematopoietic prostaglandin D synthase (hPGDS), modulators of the NFκβ pathway such as IKK inhibitors, modulators of cytokine signalling pathways such as p38 MAP kinases, PI3 kinases, JAK kinases, syk kinase, EGFR, MK-2, fyn kinases or ITK etc. . . . .

According to a preferred embodiment of the present invention, the pharmaceutically active ingredient(s) may be selected from:

muscarinic M3 receptor agonists or anticholinergic agents such as ipratropium, tiotropium, oxitropium, trospium, aclidinium, perenzepine, telenzepine and other muscarinic agonists such as e.g. those described in WO 03/035599, WO 2007/034325, WO 08/035157 or WO 2009/034432, as well as salts and/or solvates thereof;

β2-adrenoceptor agonists such as ephedrine, adrenaline, isoprenaline, metaproterenol, phenylephrine, phenylpropanolamine, pirbuterol, reproterol, rimiterol, isoetharine, carmoterol, albuterol, terbutaline, bambuterol, fenoterol, salbutamol, tulobuterol formoterol, salmeterol, and other β2-agonists such as e.g. those described in WO 04/032921, WO 05/080313, WO 05/080324, WO 05/090287, WO 05/092840 and WO 2007/010356 as well as salts and/or solvates thereof;

compounds having a dual muscarinic antagonist and β2-agonist activity such as e.g. those described in WO 2007/107828 or WO 2008/041095;

Glucocorticoid receptor agonists such as prednisone, prednisolone, flunisolide, triamcinolone acetonide, beclomethasone, budesonide, fluticasone, ciclesonide, mometasone as well as salts and/or solvates thereof;

and dual or triple combinations thereof.

Prior to use in a dry powder formulation, the pharmaceutically active ingredient should be presented for administration in a size suitable for delivery by inhalation. This may be achieved by controlled crystallization and isolation of the pharmaceutically active ingredient using for example high shear wet milling or sonocrystallisation, followed by any appropriate comminuting method, such as spiral jet milling, fluid bed jet milling, supercritical fluid processing, high pressure homogenisation, or spray drying. The particles that are so obtained typically have an average aerodynamic particle size of less than 10 μm, preferably less than 6 μm, more preferably of less than 5 μm.

The excipient used in the context of the present invention may be any physiologically acceptable excipient which can be used in the context of the inhalable formulation. As a matter of example, said excipient may be selected from monosaccharides, disaccharides, oligo- and polysaccharides. Examples of such excipient include glucose, arabinose, lactose, sucrose, maltose, dextrans. Monosaccharides or disaccharides are preferably used. More preferably, the excipient used in the context of the present invention is lactose, most preferably lactose monohydrate.

The excipient powder according to the present invention may further be made of a mixture of components comprising a component as herein before described together with other components selected from e.g. phospholipids such as phosphatidylcholine, performance modifier such as l-leucine, mannitol, or magnesium stearate. Suitable flavours, such as menthol and levomenthol, or sweeteners, such as saccharin or saccharin sodium, may be added to those formulations of the invention intended for inhaled/intranasal administration.

The excipient powder that may be used in the context of the present invention is made of particles having an average size that is less than 200 μm, preferably less than 100 μm. More preferably, the excipient powder is made of particles having an average particle size that is comprised between 10 μm and 80 μm, still more preferably between 15 and 60 μm.

According to a preferred embodiment, the medication powder dose according to the present invention comprises one or more pharmaceutically active ingredient selected from muscarinic M3 receptor agonists, β2-adrenoceptor agonists and/or glucocorticoid receptor agonists as herein before described, and lactose as the excipient.

More preferably, the medication powder dose according to the present invention comprises one or more pharmaceutically active ingredient(s) selected from ipratropium, tiotropium, oxitropium, trospium, aclidiniums, perenzepine, telenzepine, ephedrine, adrenaline, isoprenaline, metaproterenol, phenylephrine, phenylpropanolamine, pirbuterol, reproterol, rimiterol, isoetharine, carmoterol, albuterol, terbutaline, bambuterol, fenoterol, salbutamol, tulobuterol formoterol, salmeterol, prednisone, prednisolone, flunisolide, triamcinolone acetonide, beclomethasone, budesonide, fluticasone, ciclesonide, mometasone as well as salts and/or solvates thereof and lactose as the excipient.

Still more preferably, the medication powder dose according to the present invention comprises one or more pharmaceutically active ingredient(s) selected from ipratropium, tiotropium, oxitropium, trospium, aclidiniums, perenzepine, telenzepine, ephedrine, adrenaline, isoprenaline, metaproterenol, phenylephrine, phenylpropanolamine, pirbuterol, reproterol, rimiterol, isoetharine, carmoterol, albuterol, terbutaline, bambuterol, fenoterol, salbutamol, tulobuterol formoterol, salmeterol, prednisone, prednisolone, flunisolide, triamcinolone acetonide, beclomethasone, budesonide, fluticasone, ciclesonide, mometasone as well as salts and/or solvates thereof and lactose monohydrate as the excipient.

As visible on FIGS. 2 and 3, each dose carrier 15 comprises a supporting structure in the form of a rigid disc 21 having a number of through holes 23 extending from one side of the disc to the other and rigid inserts 25 defining the pockets 17, each accommodated in a respective through hole 23. Each insert 25 is cup-shaped with its external surface fitting on the internal surface of the corresponding through hole 23, whereby the insert 25 is able to axially slide in the through hole from a storage position (FIG. 2) into a dispensing position (FIG. 3). The insert 25 has a bottom wall defining the closed side of the cup shape and provided with an external flat surface 27 which, in the storage position, extends in the plane of a first side of the disc 21. At the open side of the cup shape, the insert 25 has a peripheral edge 29 substantially extending, in the storage position, in the plane of the second side of the disc 21. All the inserts 25 of a same dose carrier 15 are oriented in the same way which means that all the inserts 25 have their closed side on the same side of the disc 21.

Each dose carrier 15 also includes a pair of foils (not shown) respectively attached to the first and second faces of the disc 21 so as to hermetically enclose the inserts 25 with the powder contained therein and protect the powder from any moisture ingress and contamination until delivery. The foil applied on the second side of the disc is designed to be ruptured open by the edge 29 of the insert 25 when said insert is axially pushed from the first side toward the second side, so as to allow the powder to be exposed in a flow of air.

Referring back to FIG. 1, the through holes 23 are formed in the disc 21 according to an annular distribution wherein the holes are angularly and regularly spaced one from the other about the axis Z. The inserts 25 are thus held in the disc 21 in an annular arrangement defining a distribution of pockets 17 for the dose units 5a, 5b. It should be further noted that the two dose units 5a, 5b have corresponding or identical distributions of pockets 17, that means the same number of pockets with the same angular spacing therebetween.

The supports 7a, 7b may each comprise an anvil plate (not shown) and an airway plate (not shown) designed to be attached to the respective dose units 5a, 5b and to be rotatably mounted, together with the respective dose units, within the housing 3a, 3b. The internal structure 7 defined by the supports 7a, 7b is designed to both allow a proper extraction of the inserts 25 from their storage position into their dispensing position and provide individual paths for the inhalation airflow between the air intakes 11a and an air outlet of the mouthpiece 13a, 13b through the respective pockets 17.

On FIGS. 2 and 3, for the sake of clarity, the internal structure 7 is schematically represented as a single piece although it is not in fact. As visible on these figures, the structure 7 defines, for each pocket 17 of each dose unit 5a, 5b, a path 33 for the airflow, with a section 35 upstream the associated pocket and a section 37 downstream the same pocket. The downstream sections 37 of the respective paths 33 end up into a common duct 38 to the outlet.

In the storage position (FIG. 2), an insert 25 is fully enclosed in the associated disc 21 and, in the dispensing position (FIG. 3), it projects from the disc so as to be integral part of the walls defining the flow path 33 and expose the powder contained in the insert to the airflow. On FIG. 3, the airflow associated with the dose unit 5a is referred to as Fa and the airflow associated with the dose unit 5b is referred to as Fb.

The mechanism 9 will not be described in much detail in the present application as a similar arrangement is known from the aforementioned patent application WO 2005/002654 to which one may refer to understand more details of constitution and operation of the inhaler 1. However, it is important to note for the understanding of the present invention, that the mechanism 9 comprises a movable part 40 rotatably mounted within the housing 3a, 3b about the axis Z, said movable part having, integrally made, a lever 41 and a rotative cam 43. The cam 43 is formed as an annular portion extending essentially in a radial plane over a certain angle and having a thickness varying with the angle of rotation about the axis Z. The mechanism also has two cam followers in the form of two prodgers 45, each axially movable in accordance with the angular position of the cam 43 and each associated with a respective dose unit 5a, 5b.

The mechanism 9 is also provided with means, such as toothed wheels meshing with complementary teeth provided on the supports 7a, 7b, for rotating together the supports and the dose units 5a, 5b about the axis Z with the operation of the lever 41 over a certain angular travel.

It will be appreciated that, in the assembled configuration of the inhaler 1, the dose units 5a, 5b, the supports 7a, 7b and the mechanism 9 are enclosed in the housing 3a, 3b, the lever 41 extending out of the inner compartment defined by the housing so as to be handled by a user.

The inhaler 1 may further comprise a mouthpiece cover (not shown) rotatably supported by the housing 3a, 3b so as to be displaceable between a storage position, wherein it covers the mouthpiece 13a, 13b and the lever 41 thereby preventing access thereto and operation of the inhaler, and a use position, wherein it leaves free access to the mouthpiece and the lever.

Starting from a neutral initial position, when the lever 41 is activated, it sequentially
  (i) rotates the supports 7a, 7b together with the respective dose units 5a, 5b over the angular spacing between two successive pockets 17 so as to place one fresh pocket of each dose unit in correspondence with the respective prodger 45 and then
  (ii) simultaneously displaces, by the action of the cam 43 on the prodgers 45, the two prodgers 45 in the axial direction so as to push the inserts 25 from their storage position into their dispensing position as shown on FIGS. 2 and 3.

As the inserts 25 are pushed by the respective prodgers 45 out of the through holes 23, they burst through the protective lidding foil so as to expose properly the powder to the airflow. When the inhalation occurs, as shown on FIG. 3, the powder from the two corresponding pockets 17 is simultaneously dispensed in the respective airflows Fa, Fb which mix up downstream in the duct 38.

At the end of this operation, the lever is returned back to its initial position by means not shown on the figures without causing any further or reverse rotation of the dose units.

It will be appreciated that the annular arrangement of the pockets 17 in the dose units 5a, 5b, since the discs 21 are rotatably mounted in the housing of the inhaler, defines a sequential arrangement allowing that the content of the pockets is sequentially exposed to a flow of air for successive inhalations.

Figure 4:
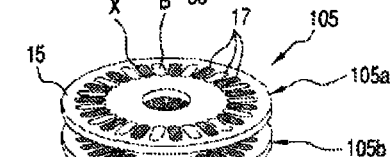
Figure 5:
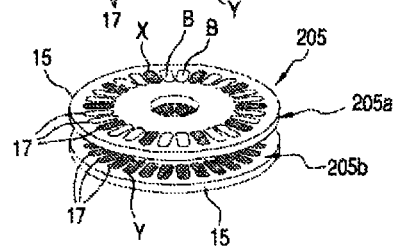

Different versions of the first embodiment of the invention are shown on FIG. 4-5, wherein packs of two dose units suitable for use within the inhaler 1 are as described above.

In the version of FIG. 4, the pack 105 includes
  a first dose unit 105a having, in an annular arrangement such as described for the dose unit 5a in reference to FIG. 1, a sequence of pockets which are alternatively blank B and inclusive of dose of a first medication powder X; and
  a second dose unit 105b having, in an annular arrangement such as described for the dose unit 5b in reference to FIG. 1, a sequence of pockets all containing a dose of a second medication powder Y, preferably different from the first medication powder X.

A "blank" pocket should be understood, in the present description, as a pocket which does not include a pharmaceutically active ingredient. A blank pocket may be an empty pocket but it may preferably be a pocket containing an excipient powder (such as lactose) without pharmaceutically active ingredient, whereby the inhalation effort and the perception of the user are not affected by the presence of blank pockets. As opposed to "blank", the term "active" may be used in some circumstances in the description below to qualify the pockets inclusive of medication powder.

The first X and second Y medication powders each may include a single pharmaceutically active ingredient or a combination of two or more pharmaceutically active ingredients.

In a first illustrative example corresponding to a preferred embodiment:
  the first medication powder X includes a single pharmaceutically active ingredient selected from the group consisting of β2-adrenoceptor agonists such as ephedrine, adrenaline, isoprenaline, metaproterenol, phenylephrine, phenylpropanolamine, pirbuterol, reproterol, rimiterol, isoetharine, carmoterol, albuterol, terbutaline, bambuterol, fenoterol, salbutamol, tulobuterol formoterol, salmeterol, and other β2-agonists such as e.g. those described in WO 04/032921, WO 05/080313, WO 05/080324, WO 05/090287, WO 05/092840 and WO 2007/010356 as well as salts thereof;
  the second medication powder Y includes a single ingredient selected from the group consisting of glucocorticoid receptor agonists such as prednisone, prednisolone, flunisolide, triamcinolone acetonide, beclomethasone dipropionate, budesonide, fluticasone, ciclesonide, mometasone as well as salts thereof.

In a second illustrative example corresponding to another preferred embodiment:

the first medication powder X includes a fixed combination of two pharmaceutically active ingredients, the first one being selected from the group consisting of β2-adrenoceptor agonists such as ephedrine, adrenaline, isoprenaline, metaproterenol, phenylephrine, phenylpropanolamine, pirbuterol, reproterol, rimiterol, isoetharine, carmoterol, albuterol, terbutaline, bambuterol, fenoterol, salbutamol, tulobuterol formoterol, salmeterol, and other β2-agonists such as e.g. those described in WO 04/032921, WO 05/080313, WO 05/080324, WO 05/090287, WO 05/092840 and WO 2007/010356 as well as salts thereof and the second one being selected from the group consisting of glucocorticoid receptor agonists such as prednisone, prednisolone, flunisolide, triamcinolone acetonide, beclomethasone dipropionate, budesonide, fluticasone, ciclesonide, mometasone as well as salts thereof;

the second medication powder Y includes a single ingredient selected from the group consisting of muscarinic M3 receptor agonists or anticholinergic agents such as ipratropium, tiotropium, oxitropium, trospium, aclidinium, perenzepine, telenzepine and other muscarinic agonists such as e.g. those described in WO 03/035599, WO 2007/034325, WO 08/035157 or WO 2009/034432, as well as salts thereof.

In a third illustrative example corresponding to another preferred embodiment:

the first medication powder X includes a combination of active ingredients which is either a combination of salmeterol xinafoate and fluticasone propionate, or a combination of budesonide and formoterol fumarate dihydrate; and the second medication powder Y includes a single ingredient selected from the group consisting of tiotropium, bromide.

With the configuration depicted with reference to FIG. 4, it is made possible to dispense two different medication powders X, Y with the same inhaler at different frequencies, the medication powder Y being dispensed at twice the frequency of the medication powder X. It is thus made possible, for example, to dispense the medication powder X twice a day (in combination with Y) and the medication powder Y four times a day (including two times in combination with X).

In the version of FIG. 5, the pack 205 includes
a first dose unit 205a having, in regularly repeated manner, a sequence of two blank pockets B and one active pocket including a dose of the first medication powder X; and
a second dose unit 205b with all pockets active containing a dose of the second medication powder Y.

It is easily conceivable that this configuration allows dispensing the pharmaceutically active ingredient(s) of powder Y with a frequency which is three times the frequency of dispensing of the pharmaceutically active ingredient(s) of powder X.

In the versions of FIGS. 6 and 7, each dose unit has two annular arrangements of pockets wherein each pocket of the first annular arrangement has, in the second annular arrangement, a corresponding pocket radially spaced therefrom at the same angular location. It should be noted that such dose units are suitable to be used within the inhaler illustrated on FIG. 1-3 provided that, the prodgers 45 are adapted to simultaneously burst the two corresponding pockets.

In the version of FIG. 6, the pack 305 includes:
a first dose unit 305a comprising:
in the first annular arrangement, which is the radially outermost arrangement, a sequence of alternatively blank pockets B and active pockets each inclusive of dose of a first medication powder X1;
in the second annular arrangement, which is the radially innermost arrangement, only active pockets each inclusive of a dose of a second medication powder X2;
a second dose unit 305b comprising:
in the first annular arrangement, which is the radially outermost arrangement, only active pockets each inclusive of a dose of a third medication powder Y1;
in the second annular arrangement, which is the radially innermost arrangement, only active pockets each inclusive of a dose of a fourth medication powder Y2.

It will be appreciated that this configuration allows dispensing the pharmaceutically active ingredients of the powders X2, Y1, Y2 at the same frequency and the pharmaceutically active ingredient of the powder X1 at half this frequency, in accordance with the following repeated sequence:

(i) dispensing of the combination X1+X2+Y1+Y2;
(ii) dispensing of the combination X2+Y1+Y2.

In the version of FIG. 7, the pack 405 includes:
a first dose unit 405a comprising:
in the first annular arrangement, which is the radially outermost arrangement, a sequence of alternatively blank pockets B and active pockets each inclusive of dose of a first medication powder X1;
in the second annular arrangement, which is the radially innermost arrangement, a sequence of alternatively blank pockets B and active pockets each inclusive of dose of a first medication powder X2, the blank pockets of the second arrangement being angularly offset from those of the first arrangement such that each pair of two corresponding pockets from the two arrangements has a blank pocket and an active pocket, alternatively with X1 and X2;
a second dose unit 405b comprising:
in the first annular arrangement, which is the radially outermost arrangement, only active pockets each inclusive of a dose of a third medication powder Y1;
in the second annular arrangement, which is the radially innermost arrangement, only active pockets each inclusive of a dose of a fourth medication powder Y2.

It will be appreciated that this configuration allows dispensing the pharmaceutically active ingredients of the powders X1, X2 at a first frequency and the pharmaceutically active ingredients of the powders Y1, Y2 at a second frequency which is twice the first frequency, in accordance with the following repeated sequence:

(iii) dispensing of the combination X1+Y1+Y2;
(iv) dispensing of the combination X2+Y1+Y2.

In all the above-described configurations, the doses of medication powder of the first dose unit are regularly distributed in the pockets according to a sequence of identical groups, each group including at least one blank pocket and one pocket containing a dose of medication powder.

With reference to FIG. 8, a second embodiment of the invention will now be described which relates to an inhalation device of the type disclosed for example in the patent application WO 004/011070. With this device, combination of medicaments can be dispensed from a pair of dose units including elongated and flexible strips.

As also schematically represented on FIG. 8, which shows a pack 505 of dose units 505a, 505b in accordance with the invention, a typical dose unit 505b suitable for use within such inhalers comprises a dose carrier in the form of an elongated strip 515 formed with successive cavities 517. Said cavities 517 that define pockets for containing inhalation powder are arranged along the main direction Δ of the strip 515. The dose unit 505b also comprises a lid sheet 524 which is initially sealed to the strip 515 in order to hermetically close the pockets and which can be peeled apart from the strip 515.

The elongated strip 515 associated with the lid sheet 524 is suitable to be shaped into a winding and adapted to be, in an inhaler of the type known from WO 004/011070, step by step unwound and advanced along the main direction Δ while the lid sheet 524 being progressively peeled apart from the strip 515, whereby the content of successive pockets can be exposed to an inhalation airflow.

Likewise, the other dose unit 505a of the pack 505 shown on FIG. 8 is adapted to be used in an inhaler of the same type, in association with the dose unit 505b for dispensing combination of medication powders.

In accordance with the invention, the first dose unit 505a includes an arrangement of successive pockets along the main direction Δ, said arrangement comprising alternatively a blank pocket B and an active pocket including the first medication powder X.

The second dose unit 505b of the pack 505 according to the invention includes an arrangement of successive pockets along the main direction Δ, said arrangement comprising only active pockets including the second active powder Y.

Like the configuration shown on FIG. 4, the embodiment of FIG. 8 allows dispensing of two different medication powders X, Y with the same inhaler at different frequencies. In this specific example, the medication powder Y is dispensed at twice the frequency of the medication powder X, the medication powder X being dispensed in combination with the medication powder Y.

It will be appreciated that, irrespective of the type of inhaler and the type of associated dose carrier, the invention provides means to achieve a dispensing of different medication powders at different frequencies with one single inhaler, according to a repeatable sequence.

The invention claimed is:

1. A dose unit for a dry powder inhaler comprising:
   a dose carrier (15; 515, 524) including a plurality of pockets (17; 517) each adapted to contain a dose of medication powder suitable for inhalation, said pockets being sequentially arranged such that the content of the pockets (17; 517) can be sequentially exposed to a flow of air (Fa) for successive inhalations and
   a plurality of medication powder doses (X; X1, X2) arranged in said pockets (17; 517) of the dose carrier (15),
   wherein the doses are regularly distributed in the pockets according to a sequence of identical groups, each group including at least one blank pocket (B) containing an excipient powder without pharmaceutically active ingredient and one pocket containing a dose of medication powder (X; X1, X2).

2. A dose unit according to claim 1, characterized in that the dose carrier (15) comprises a disc-shaped supporting structure (21) and the pockets (17) are held in an annular arrangement in the supporting structure, said supporting structure being adapted to be rotatably mounted in the dry powder inhaler (1) so as to sequentially expose the content of the pockets (17).

3. A dose unit according to claim 2, characterized in that the disc-shaped supporting structure (21) includes an annular arrangement of through holes (23) and that the dose carrier (15) further comprises rigid inserts (25) defining the pockets (17), each of said inserts being slidably accommodated in the respective through-hole (23) in a storage position and is adapted to be displaced by prodgers (45) from said storage position into a dispensing position projecting from the disc-shaped supporting structure (21) wherein the content of the pocket is exposed to the airflow (Fa).

4. A dose unit according to claim 1, characterized in that the dose carrier comprises an elongated strip (515) formed with successive cavities (517) defining the pockets arranged along the main direction (Δ) of the strip.

5. A dose unit according to claim 4, characterized in that said elongated strip (515) is flexible and shaped into a winding whereby the strip is adapted to be unwound in the dry powder inhaler so as to sequentially expose the content of the pockets (517).

6. A dose unit according to claim 1, characterized in that each of said identical groups is constituted of one pocket containing a dose of medication powder (X; X1, X2) and one blank pocket (B), whereby the pockets of the dose unit are alternatively blank (B) and inclusive of a dose of medication powder (X; X1, X2).

7. A dose unit according to claim 1, characterized in that the medication powder (X; X1, X2) includes a single pharmaceutically active ingredient.

8. A dose unit according to claim 7, characterized in that said single pharmaceutically active ingredient is selected from the group consisting of muscarinic M3 receptor agonists or anticholinergic agents, β2-adrenoceptor agonists, compounds having a dual muscarinic antagonist and β2-agonist activity and glucocorticoid receptor agonists.

9. A dose unit according to claim 8 wherein said single pharmaceutically active ingredient is selected from the group consisting of ipratropium, tiotropium, oxitropium, trospium, aclidiniums, perenzepine, telenzepine, ephedrine, adrenaline, isoprenaline, metaproterenol, phenylephrine, phenylpropanolamine, pirbuterol, reproterol, rimiterol, isoetharine, carmoterol, albuterol, terbutaline, bambuterol, fenoterol, salbutamol, tulobuterol formoterol, salmeterol, prednisone, prednisolone, flunisolide, triamcinolone acetonide, beclomethasone, budesonide, fluticasone, ciclesonide, mometasone as well as salts and/or solvates thereof.

10. A dose unit according to claim 1, characterized in that the medication powder (X; X1, X2) includes a combination of pharmaceutically active ingredients.

11. A dose unit according to claim 10, characterized in that said combination of pharmaceutically active ingredients is a combination of a β2-adrenoceptor agonist and a glucocorticoid receptor agonist.

12. A dose unit according to claim 11 wherein said combination of pharmaceutically active ingredients is a combination of salmeterol xinafoate and fluticasone propionate or a combination of budesonide and formoterol fumarate dehydrate.

13. A pack including a first dose unit (105a; 205a; 305a; 405a; 505a) according to any one of claims 1 to 12 and a second dose unit (105b; 205b; 305b; 405b; 505b) for a dry powder inhaler comprising a dose carrier (15; 515) including a plurality of pockets (17; 517) adapted to contain a dose of a medication powder suitable for inhalation, said pockets being sequentially arranged such that the content of the pockets can be sequentially exposed to a flow of air (11) for successive inhalations and a plurality of medication powder doses (Y; Y1, Y2) arranged in the respective pockets (17;

517) of the dose carrier (15; 515) such that all the pockets of the second dose unit (105b; 205b; 305b; 405b; 505b) are inclusive of a medication powder dose (Y; Y1, Y2).

14. A pack according to claim 13, characterized in that the dose carrier (15; 515) of the first dose unit (105a; 205a; 305a; 405a; 505a) and the dose carrier (15; 515) of the second dose unit (105b; 205b; 305b; 405b; 505b) have an identical distribution of pockets (17; 517).

15. A pack according to claim 13, characterized in that the medication powder (Y) of the second dose unit (105a; 205a; 505a) includes a single pharmaceutically active ingredient.

16. A pack according to claim 15, characterized in that said single pharmaceutically active ingredient is selected from the group consisting of muscarinic M3 receptor agonists or anticholinergic agents, β2-adrenoceptor agonists, compounds having a dual muscarinic antagonist and β2-agonist activity and glucocorticoid receptor agonists.

17. A pack according to claim 16 wherein said single pharmaceutically active ingredient is selected from the group consisting of ipratropium, tiotropium, oxitropium, trospium, aclidiniums, perenzepine, telenzepine, ephedrine, adrenaline, isoprenaline, metaproterenol, phenylephrine, phenylpropanolamine, pirbuterol, reproterol, rimiterol, isoetharine, carmoterol, albuterol, terbutaline, bambuterol, fenoterol, salbutamol, tulobuterol formoterol, salmeterol, prednisone, prednisolone, flunisolide, triamcinolone acetonide, beclomethasone, budesonide, fluticasone, ciclesonide, mometasone as well as salts and/or solvates thereof.

18. A pack according to claim 13, characterized in that the medication powder (Y) of the second dose unit (105a; 205a; 505a) includes a combination of pharmaceutically active ingredients.

19. A dry powder inhaler for administering medication powder to a patient, comprising a pack (105; 205; 305; 405; 505) according to claim 13 and means (9) for simultaneously exposing in an inhalation airflow (Fa, Fb) the respective contents of a pocket of the first dose unit (105a; 205a; 305a; 405a; 505a) and a corresponding pocket of the second dose unit (105b; 205b; 305b; 405b; 505b).

* * * * *